United States Patent
Gadgil et al.

(10) Patent No.: US 11,938,202 B2
(45) Date of Patent: Mar. 26, 2024

(54) PERSONAL CLEANSING SOAP BAR COMPOSITION

(71) Applicant: Dow Global Technologies LLC, Midland, MI (US)

(72) Inventors: Sandeep S. Gadgil, Thane (IN); Rishikesh Deshmukh, Navi Mumbai (IN); Deepak Dandekar, Maharashtra (IN)

(73) Assignee: Dow Global Technologies LLC, Midland, MI (US)

( * ) Notice: Subject to any disclaimer, the term of this patent is extended or adjusted under 35 U.S.C. 154(b) by 473 days.

(21) Appl. No.: 17/055,150

(22) PCT Filed: Jun. 3, 2019

(86) PCT No.: PCT/US2019/035108
§ 371 (c)(1),
(2) Date: Nov. 13, 2020

(87) PCT Pub. No.: WO2019/240968
PCT Pub. Date: Dec. 19, 2019

(65) Prior Publication Data
US 2021/0361538 A1  Nov. 25, 2021

(30) Foreign Application Priority Data
Jun. 11, 2018 (IN) .............................. 201841021719

(51) Int. Cl.
| | | |
|---|---|---|
| *A61Q 19/10* | (2006.01) | |
| *A61K 8/02* | (2006.01) | |
| *A61K 8/25* | (2006.01) | |
| *A61K 8/81* | (2006.01) | |
| *A61K 8/895* | (2006.01) | |

(52) U.S. Cl.
CPC .......... *A61K 8/0216* (2013.01); *A61K 8/8147* (2013.01); *A61K 8/895* (2013.01); *A61Q 19/10* (2013.01); *A61K 2800/21* (2013.01); *A61K 2800/51* (2013.01); *A61K 2800/594* (2013.01); *A61K 2800/805* (2013.01)

(58) Field of Classification Search
CPC ....................................................... A61Q 19/00
See application file for complete search history.

(56) References Cited

U.S. PATENT DOCUMENTS

| | | | |
|---|---|---|---|
| 4,618,645 A | 10/1986 | Bauman et al. | |
| 5,952,276 A * | 9/1999 | de Ferran | C11D 9/36 510/447 |
| 6,013,682 A * | 1/2000 | Dalle | C08J 3/03 528/31 |
| 6,348,855 B1 | 2/2002 | Ishiguro | |
| 6,362,145 B1 | 3/2002 | Littau et al. | |
| 6,395,790 B1 | 5/2002 | Creutz et al. | |
| 8,618,035 B2 | 12/2013 | Lai et al. | |
| 8,771,657 B2 | 7/2014 | Tativana | |
| 9,090,798 B2 | 7/2015 | Bekemeier | |
| 2006/0080734 A1 | 4/2006 | Chung | |
| 2007/0042919 A1 | 2/2007 | Dalton | |
| 2011/0064683 A1 | 3/2011 | Jordan et al. | |
| 2011/0064688 A1 | 3/2011 | Jordan et al. | |
| 2011/0305653 A1 | 12/2011 | Jordan | |
| 2014/0302103 A1* | 10/2014 | Carter | A61K 9/107 424/401 |

OTHER PUBLICATIONS

Sibilia, "A Guide to Materials Characterization and Chemical Analysis." 1988, p. 81-84.

* cited by examiner

Primary Examiner — Robert T. Crow
Assistant Examiner — John P Nguyen
(74) *Attorney, Agent, or Firm* — Thomas S. Deibert

(57) ABSTRACT

A personal cleansing soap bar composition is provided, comprising: a soap; an aqueous ethylene acrylic acid copolymer dispersion; a silicone copolymer emulsion with an internal phase viscosity at 25° C. of $\geq 100 \times 10^6$ mm$^2$/sec; wherein the personal cleansing soap bar is a solid.

10 Claims, No Drawings

PERSONAL CLEANSING SOAP BAR COMPOSITION

The present invention relates to a personal cleansing soap bar composition. In particular, the present invention relates to a personal cleansing soap bar composition, comprising: a soap; an aqueous ethylene acrylic acid copolymer dispersion; a silicone copolymer emulsion with an internal phase viscosity at 25° C. of $\geq 100 \times 10^6$ mm$^2$/sec; wherein the personal cleansing soap bar is a solid.

Finishing milled personal cleansing soap bars are conventionally prepared from soap noodles having a total fatty matter (TFM) content of more than 70 wt %, 10-14 wt % water and other components (e.g., titanium dioxide, surfactant and fragrance). Currently milled bars have a typical water content of about 8 to 15 wt % and had non-milled bars have a water content of 20 to 25 wt %.

Personal cleansing soap bars of varying compositions are known. Conventional personal cleansing soap bars are conventionally formulated with a variety of additives to impart benefits that are inherent to the soap.

Conventional personal cleansing soap bars contain at least one soap (i.e., a monovalent sodium, potassium, ammonium and alkanol ammonium salts of monocarboxylic fatty acids) and optionally one or more adjuvants such as moisturizers, humectants, antibacterial agents, water, fillers, polymers, dyes, fragrances, etc., to enhance the cleansing and skin conditioning properties of the soap bar.

A variety of personal soap bar compositions have been disclosed, for example, a personal care cleansing composition in solid form is disclosed by Schmit et al. in U.S. Patent Application Publication No. 20070042919. Schmit et al disclose a personal care cleansing composition in solid form having enhanced skin feel attributes comprising a cleansing ingredient having at least about 60 wt % of a soap, 0.03 to 1.5 wt % of a quaternary ammonium compound having the structural formula

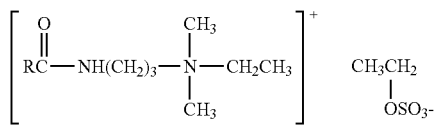

wherein R is a C$_{6-26}$ alkyl, alkenyl, alkadienyl or alkapolyneyl radical, either straight or branched chain and mixtures thereof, from 4 wt % to 8 wt % of a free fatty acid having an alkyl group of from 8 to 22 carbon atoms, and wherein the ratio of said free fatty acid to said quaternary is from 4:1 to 195:1.

Notwithstanding, there remains a continuing need for new personal cleansing soap bars offering exceptional sensory benefits is use.

The present invention provides a personal cleansing soap bar composition, comprising: 60 to 90 wt % of a soap; 0.1 to 0.6 wt % of an aqueous ethylene acrylic acid copolymer dispersion; 0.1 to 0.6 wt % of a silicone copolymer emulsion with an internal phase viscosity at 25° C. of $\geq 100 \times 10^6$ mm$^2$/sec; wherein the personal cleansing soap bar is a solid.

The present invention provides a personal cleansing soap bar composition, comprising: 60 to 90 wt % of a soap; 0.1 to 0.6 wt % of an aqueous ethylene acrylic acid copolymer dispersion; 0.1 to 0.6 wt % of a silicone copolymer emulsion with an internal phase viscosity at 25° C. of $\geq 100 \times 10^6$ mm$^2$/sec; 0.1 to 5 wt % of a humectant; 0.05 to 2 wt % of a processing aid; 0.01 to 0.5 wt % of a chelating agent; and 0.1 to 10 wt % of additional water; wherein the personal cleansing soap bar is a solid.

The present invention provides a method of making a personal cleansing soap bar composition, comprising: providing a soap; providing an aqueous dispersion comprising an ethylene acrylic acid copolymer; providing a silicone copolymer emulsion with an internal phase viscosity of $\geq 100 \times 10^6$ mm$^2$/sec; mixing the soap, the aqueous dispersion, and the silicone copolymer emulsion to form a combination; milling the combination; extruding the milled combination; and stamping the extruded material to provide the personal cleansing soap bar.

DETAILED DESCRIPTION

We have surprisingly found that personal cleansing soap bars containing a synergistic combination of an aqueous ethylene acrylic acid copolymer dispersion and a silicone copolymer emulsion provide exceptional in use sensory benefit performance with a statistically significant enhancement for in wash feel and moisture feel, without impairing sensory benefit performance for foam quality, foam volume, after wash feel and rinseability.

Unless otherwise indicated, ratios, percentages, parts, and the like are by weight.

As used herein, unless otherwise indicated, the phrase "molecular weight" or Mw refers to the weight average molecular weight as measured in a conventional manner with gel permeation chromatography (GPC) and poly(ethylene oxide) standards. GPC techniques are discussed in detail in Modem Size Exclusion Chromatography, W. W. Yau, J. J. Kirkland, D. D. Bly; Wiley-lnterscience, 1979, and in A Guide to Materials Characterization and Chemical Analysis, J. P. Sibilia; VCH, 1988, p. 81-84. Molecular weights are reported herein in units of Daltons.

The term "cosmetically acceptable" as used herein and in the appended refers to ingredients typically used in personal care compositions, and is intended to underscore that materials that are toxic when present in the amounts typically found in personal care compositions are not contemplated as part of the present invention.

The term "structural units" as used herein and in the appended claims refers to the remnant of the indicated monomer; thus a structural unit of acrylic acid is illustrated:

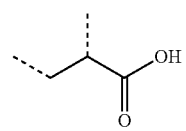

where the dotted lines represent the points of attachment to the polymer backbone.

Preferably, the personal cleansing soap bar composition of the present invention, comprises: 60 to 90 wt % (preferably, 65 to 85 wt %; more preferably, 70 to 80 wt %) of a soap; 0.1 to 0.6 wt % (preferably, 0.2 to 0.4 wt %; more preferably, 0.25 to 0.35 wt %; most preferably, 0.275 to 0.325 wt %) of an aqueous ethylene acrylic acid copolymer dispersion; 0.1 to 0.6 wt % (preferably, 0.2 to 0.4 wt %; more preferably, 0.25 to 0.35 wt %; most preferably, 0.275 to 0.325 wt %) of a silicone copolymer emulsion with an internal phase viscosity at 25° C. of $\geq 100 \times 10^6$ mm$^2$/sec (preferably, $\geq 120 \times 10^6$ mm$^2$/sec; more preferably, $\geq 150 \times 10^6$ mm$^2$/sec); 0 to 5 wt % (preferably, 0.1 to 2.5 wt %; more preferably, 0.25 to 2 wt %; still more preferably, 0.5 to 1.5 wt %; most preferably, 0.75 to 1.25 wt %) of a humectant; 0 to 2 wt % (preferably, 0.05 to 2 wt %; more preferably, 0.1 to 1.5 wt %; still more preferably, 0.25 to 1.25 wt %; most preferably, 0.5 to 1 wt %) of a processing aid; 0 to 0.5 wt % (preferably, 0.01 to 0.3 wt %; more preferably, 0.05 to 0.25 wt %; still more preferably, 0.075 to 0.2 wt %; most preferably, 0.1 to 0.15 wt %) of a chelating agent; and 0 to 10 wt % (preferably, 1 to 7.5 wt %; more preferably 2 to 6 wt %; most preferably, 3 to 5 wt %) of additional water; wherein the personal cleansing soap bar is a solid.

Preferably, the personal cleansing soap bar composition of the present invention, comprises: 60 to 90 wt % (preferably, 65 to 85 wt %; more preferably, 70 to 80 wt %) of a soap. More preferably, the personal cleansing soap bar composition of the present invention, comprises: 60 to 90 wt % (preferably, 65 to 85 wt %; more preferably, 70 to 80 wt %) of a soap, wherein the soap is selected from the group consisting of monovalent salts of monocarboxylic fatty acids having counterions selected from the group consisting of sodium, potassium, ammonium and alkanol ammonium ions. Still more preferably, the personal cleansing soap bar composition of the present invention, comprises: 60 to 90 wt % (preferably, 65 to 85 wt %; more preferably, 70 to 80 wt %) of a soap; wherein the soap is an alkali (preferably, sodium) salt of a fatty acid from at least one of an animal fat and a vegetable oil. Yet more preferably, the personal cleansing soap bar composition of the present invention, comprises: 60 to 90 wt % (preferably, 65 to 85 wt %; more preferably, 70 to 80 wt %) of a soap; wherein the soap is an alkali (preferably, sodium) salt of a fatty acid from at least one of palm oil, palm kernel oil, castor oil, rice bran oil, sunflower oil, coconut oil, soybean oil, peanut oil, tallow, lard, fish oil and blends thereof. Yet still more preferably, the personal cleansing soap bar composition of the present invention, comprises: 60 to 90 wt % (preferably, 65 to 85 wt %; more preferably, 70 to 80 wt %) of a soap; wherein the soap is an alkali (preferably, sodium) salt of a fatty acid from a 40:60 to 97:3 blend of oils and fats (preferably, the blend of oils and fats is selected from a blend of palm and palm kernel oils and a blend of palm and coconut kernel oils). Most preferably, the personal cleansing soap bar composition of the present invention, comprises: 60 to 90 wt % (preferably, 65 to 85 wt %; more preferably, 70 to 80 wt %) of a soap; wherein the soap is an alkali (preferably, sodium) salt of a fatty acid from an 80:20 blend of palm oil and palm kernel oil.

Preferably, the personal cleansing soap bar composition of the present invention, comprises: 0.1 to 0.6 wt % (preferably, 0.2 to 0.4 wt %; more preferably, 0.25 to 0.35 wt %; most preferably, 0.275 to 0.325 wt %) of an aqueous ethylene acrylic acid copolymer dispersion, comprising: an ethylene acrylic acid copolymer; and water. More preferably, the personal cleansing soap bar composition of the present invention, comprises: 0.1 to 0.6 wt % (preferably, 0.2 to 0.4 wt %; more preferably, 0.25 to 0.35 wt %; most preferably, 0.275 to 0.325 wt %) of an aqueous ethylene acrylic acid copolymer dispersion, comprising: an ethylene acrylic acid copolymer and water; wherein the ethylene acrylic acid copolymer, comprises 15 to 30 wt % (more preferably, 17 to 25 wt %; most preferably, 19 to 21 wt %), based on weight of the ethylene acrylic acid copolymer, of structural units of acrylic acid; and 70 to 85 wt % (more preferably, 75 to 83 wt %; most preferably, 79 to 81 wt %), based on weight of the ethylene acrylic acid copolymer, of structural units of ethylene. Most preferably, the personal cleansing soap bar composition of the present invention, comprises: 0.1 to 0.6 wt % (preferably, 0.2 to 0.4 wt %; more preferably, 0.25 to 0.35 wt %; most preferably, 0.275 to 0.325 wt %) of an aqueous ethylene acrylic acid copolymer dispersion, comprising: an ethylene acrylic acid copolymer and water; wherein the ethylene acrylic acid copolymer, comprises 15 to 30 wt % (more preferably, 17 to 25 wt %; most preferably, 19 to 21 wt %), based on weight of the ethylene acrylic acid copolymer, of structural units of acrylic acid; and 70 to 85 wt % (more preferably, 75 to 83 wt %; most preferably, 79 to 81 wt %), based on weight of the ethylene acrylic acid copolymer, of structural units of ethylene; and wherein the aqueous acrylic acid copolymer dispersion comprises 10 to 50 wt % (more preferably, 15 to 40 wt %; still more preferably, 20 to 30 wt %; most preferably, 23 to 27 wt %), based on the weight of the aqueous acrylic acid copolymer dispersion, of solids.

Preferably, the aqueous ethylene acrylic acid copolymer dispersion, further comprises a neutralizing agent. More preferably, the aqueous ethylene acrylic acid copolymer dispersion, further comprises a neutralizing agent; wherein the neutralizing agent is selected from the group consisting of ammonia, potassium hydroxide, sodium hydroxide and mixtures thereof. Still more preferably, the aqueous ethylene acrylic acid copolymer dispersion, further comprises a neutralizing agent; wherein the neutralizing agent includes sodium hydroxide. Most preferably, the aqueous ethylene acrylic acid copolymer dispersion, further comprises a neutralizing agent; wherein the neutralizing agent is sodium hydroxide.

Preferably, the personal cleansing soap bar composition of the present invention, comprises: 0.1 to 0.6 wt % (preferably, 0.2 to 0.4 wt %; more preferably, 0.25 to 0.35 wt %; most preferably, 0.275 to 0.325 wt %) of an aqueous ethylene acrylic acid copolymer dispersion, comprising: an ethylene acrylic acid copolymer, a neutralizing agent and water. More preferably, the personal cleansing soap bar composition of the present invention, comprises: 0.1 to 0.6 wt % (preferably, 0.2 to 0.4 wt %; more preferably, 0.25 to 0.35 wt %; most preferably, 0.275 to 0.325 wt %) of an aqueous ethylene acrylic acid copolymer dispersion, comprising: an ethylene acrylic acid copolymer, a neutralizing agent and water; wherein the ethylene acrylic acid copolymer, comprises 15 to 30 wt % (more preferably, 17 to 25 wt %; most preferably, 19 to 21 wt %), based on weight of the ethylene acrylic acid copolymer, of structural units of acrylic acid; and 70 to 85 wt % (more preferably, 75 to 83 wt %; most preferably, 79 to 81 wt %), based on weight of the ethylene acrylic acid copolymer, of structural units of ethylene; and wherein at least some (preferably, at least 70%; more preferably, at least 75; still more preferably, at least 80%; most preferably, at least 85%) of the structural units of acrylic acid have been neutralized by the neutralizing agent (preferably, sodium hydroxide). Most preferably, the personal cleansing soap bar composition of the present invention, comprises: 0.1 to 0.6 wt % (preferably, 0.2 to 0.4 wt %; more preferably, 0.25 to 0.35 wt %; most preferably, 0.275 to 0.325 wt %) of an aqueous ethylene acrylic acid copolymer dispersion, comprising: an ethylene acrylic acid copolymer, a neutralizing agent and water; wherein the ethylene acrylic acid copolymer, comprises 15 to 30 wt % (more preferably, 17 to 25 wt %; most preferably, 19 to 21 wt %), based on weight of the ethylene acrylic acid copolymer, of structural units of acrylic acid; and 70 to 85 wt % (more preferably, 75 to 83 wt %; most preferably, 79 to 81 wt %), based on weight of the ethylene acrylic acid copolymer, of structural units of ethylene; wherein at least some (preferably, at least 70%; more preferably, at least 75; still more preferably, at least 80%; most preferably, at least 85%) of the structural units of acrylic acid have been neutralized by the neutralizing agent (preferably, sodium hydroxide); and wherein the aqueous acrylic acid copolymer dispersion comprises 10 to 50 wt % (more preferably, 15 to 40 wt %; still more preferably, 20 to 30 wt %; most preferably, 23 to 27 wt %), based on the weight of the aqueous acrylic acid copolymer dispersion, of solids.

Preferably, the personal cleansing soap bar composition of the present invention, comprises: 0.1 to 0.6 wt % (preferably, 0.2 to 0.4 wt %; more preferably, 0.25 to 0.35 wt %; most preferably, 0.275 to 0.325 wt %) of a silicone copolymer emulsion with an internal phase viscosity at 25° C. of ≥100×10$^6$ mm$^2$/sec (preferably, ≥120×10$^6$ mm$^2$/sec; more preferably, ≥150×10$^6$ mm$^2$/sec). To measure the internal phase viscosity of the silicone copolymer emulsion, one must first break the polymer from the emulsion. By way of example, the following procedure can be used to break the polymer from the emulsion: 1) add 10 grams of a silicone copolymer emulsion sample to 15 milliliters of isopropyl alcohol; 2) mix well with a spatula; 3) decant the isopropyl alcohol; 4) add 10 milliliters of acetone and knead the polymer with spatula; 5) decant the acetone; 6) place polymer in an aluminum container and flatten/dry with a paper towel; and 7) dry for two hours in an 80° C. The polymer can then be tested using any known rheometer, such as, for example, a CarriMed, Haake, or Monsanto rheometer, which operates in the dynamic shear mode. The internal phase viscosity values can be obtained by recording the dynamic viscosity (n') at a 9.900×10$^{-3}$ Hz frequency point.

Preferably, the silicone copolymer emulsion has an average particle size of ≤1 micron (wherein the average particle size is measured as D50-Microtrac). More preferably, the silicone copolymer emulsion has an average particle size of ≤0.7 micron (wherein the average particle size is measured as D50-Microtrac). Preferably, the silicone copolymer emulsion comprises: a silicone copolymer, at least one surfactant and water.

Preferably, the silicone copolymer emulsion comprises a silicone copolymer, wherein the silicone copolymer is an addition reaction product, in the presence of a metal containing catalyst, of: (a) a polysiloxane with reactive groups on both termini and (b) at least one compound having an average of 1 to 2 moieties capable of reaction with the termini of the polysiloxane.

Preferably, the silicone copolymer emulsion comprises a silicone copolymer, wherein the silicone copolymer is an addition reaction product, in the presence of a metal containing catalyst, of: (a) a polysiloxane with reactive groups, R$_1$, on both termini and (b) at least one compound having an average of 1 to 2 moieties capable of reaction with the reactive groups, R$_1$, of the polysiloxane; wherein the polysiloxane has the following formula:

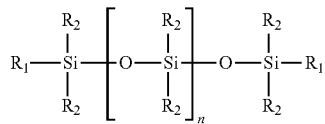

wherein each R$_1$ is independently selected from a group capable of reacting by chain addition reaction (preferably, wherein R$_1$ is selected from the group consisting of a hydrogen atom, an aliphatic group with an ethylenic unsaturation (e.g., a vinyl, an allyl, a hexenyl), a hydroxyl group, an alkoxyl group (e.g., a methoxyl, ethoxyl, a propoxyl), an acetoxyl group, an amino group, and an alkylamino group; more preferably, wherein R$_1$ is a hydrogen or an aliphatic group with an ethylenic unsaturation; most preferably, wherein R$_1$ is a hydrogen); wherein each R$_2$ is independently selected from the group consisting of an ether, a hydroxyl, an amine, a carboxyl, a thiol, an ester, a sulfonate, an alkyl, a cycloalkyl, an aryl and an alkylaryl (preferably, R$_2$ is selected from the group consisting of an alkyl, a cycloalkyl, an aryl and an alkylaryl; more preferably, R$_2$ is a methyl group)(optionally, 0 to 10 mol % (preferably, 0 to 2 mol %) of the R$_2$ groups may be a group as described for R$_1$, to impart a small amount of branching into the silicone copolymer); n is an average number selected such that the polysiloxane has a viscosity at 25° C. of 1 mm$^2$/sec to 1×10$^6$ mm$^2$/sec; and wherein the at least one compound (b) is selected from the group consisting of (silicone compounds and non-silicone compounds) having an average of 1 to 2 aliphatic groups with an ethylenic unsaturation.

Preferably, the silicone copolymer emulsion comprises at least one surfactant, wherein the at least one surfactant is selected from the group consisting of non-ionic surfactants, cationic surfactants, anionic surfactants, alkyl polysaccharide surfactants, amphoteric surfactants and mixtures thereof. More preferably, the silicone copolymer emulsion comprises at least one surfactant, wherein the at least one surfactant includes at least one non-ionic surfactant. Most preferably, the silicone copolymer emulsion comprises at least one surfactant, wherein the at least one surfactant includes at least one non-ionic surfactant, wherein the at least one non-ionic surfactant is a fatty alcohol ethoxylate according to the general structure

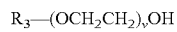

wherein R$_3$ is a straight or branched, saturated or unsaturated alkyl chain with 10 to 24 carbon atoms that may be substituted with one or more hydroxyl groups; and v is an average integer between 3 and 200 (more preferably, wherein the fatty alcohol ethoxylate is selected from the group consisting of C$_{12-13}$ Pareth-3, C$_{12-13}$ Pareth-7, C$_{12-13}$ Pareth-9, C$_{12-13}$ Pareth-10, C$_{12-13}$ Pareth-15, C$_{12-13}$ Pareth-23, Ceteareth-20, Ceteareth-30, Steareth-20, Steareth-30, Ceteth-20, Ceteth-25, Ceteth-30, Ceteth-35, Ceteth-40, Oleth-10, Oleth-20, Oleth-25, Oleth-30, Oleth-35, Oleth-40, Oleth-50, Oleth-100 and mixtures thereof; still more preferably, wherein the fatty alcohol ethoxylate is selected from the group consisting of C$_{12-13}$ Pareth-3, C$_{12-13}$ Pareth-7, C$_{12-13}$ Pareth-9, C$_{12-13}$ Pareth-10, C$_{12-13}$ Pareth-15, C$_{12-13}$ Pareth-23 and mixtures thereof; most preferably, wherein the fatty alcohol ethoxylate is a mixture of C$_{12-13}$ Pareth-3 and C$_{12-13}$ Pareth-23).

The metal containing catalysts used in preparation of the silicone copolymer are known in the art. Generally, the metal containing catalysts are materials containing metals such as platinum, rhodium, tin, titanium, copper, lead, etc.

Preferably, the personal cleansing soap bar composition of the present invention, is a solid. As used herein, the term "soap bar" refers to a unit of solid soap after it is made into a shape suitably stable under atmospheric conditions of 1 atm and 20° C.

Preferably, the personal cleansing soap bar composition of the present invention, further comprises: 0 to 5 wt % (preferably, 0.1 to 2.5 wt %; more preferably, 0.25 to 2 wt %; still more preferably, 0.5 to 1.5 wt %; most preferably, 0.75 to 1.25 wt %) of a humectant. More preferably, the personal cleansing soap bar composition of the present invention, comprises 0.1 to 5 wt % (preferably, 0.25 to 2 wt %; more preferably, 0.5 to 1.5 wt %; most preferably, 0.75 to 1.25 wt %) of a humectant. Still more preferably, the personal cleansing soap bar composition of the present invention, comprises 0.1 to 5 wt % (preferably, 0.25 to 2 wt %; more preferably, 0.5 to 1.5 wt %; most preferably, 0.75 to 1.25 wt %) of a humectant; wherein the humectant is a polyhydric alcohol selected from the group consisting of glycerin, sorbitol, propylene glycol, butylene glycol, hexylene glycol, ethoxylated glucose, 1,2-hexane diol, hexanetriol, dipropylene glycol, erythritol, trehalose, diglycerin, xylitol, maltitol, maltose, glucose, fructose and mixtures thereof. Yet more preferably, the personal cleansing soap bar composition of the present invention, comprises 0.1 to 5 wt % (preferably, 0.25 to 2 wt %; more preferably, 0.5 to 1.5 wt %; most preferably, 0.75 to 1.25 wt %) of a humectant; wherein the humectant includes glycerin. Most preferably, the personal cleansing soap bar composition of the present invention, comprises 0.1 to 5 wt % (preferably, 0.25 to 2 wt %; more preferably, 0.5 to 1.5 wt %; most preferably, 0.75 to 1.25 wt %) of a humectant; wherein the humectant is glycerin.

Preferably, the personal cleansing soap bar composition of the present invention, further comprises: 0 to 2 wt % (preferably, 0.05 to 2 wt %; more preferably, 0.1 to 1.5 wt %; still more preferably, 0.25 to 1.25 wt %; most preferably, 0.5 to 1 wt %) of a processing aid. More preferably, the personal cleansing soap bar composition of the present invention, comprises: 0.05 to 2 wt % (preferably, 0.1 to 1.5 wt %; more preferably, 0.25 to 1.25 wt %; most preferably, 0.5 to 1 wt %) of a processing aid. Still more preferably, the personal cleansing soap bar composition of the present invention, comprises: 0.05 to 2 wt % (preferably, 0.1 to 1.5 wt %; more preferably, 0.25 to 1.25 wt %; most preferably, 0.5 to 1 wt %) of a processing aid; wherein the processing aid is an inorganic powdery material selected from the group consisting of talc, calcite, kaolin, silicon dioxide, titanium dioxide, diatomaceous earth and mixtures thereof. Yet more preferably, the personal cleansing soap bar composition of the present invention, comprises: 0.05 to 2 wt % (preferably, 0.1 to 1.5 wt %; more preferably, 0.25 to 1.25 wt %; most preferably, 0.5 to 1 wt %) of a processing aid; wherein the processing aid is selected from the group consisting of talc, calcite, titanium dioxide and mixtures thereof. Most preferably, the personal cleansing soap bar composition of the present invention, comprises: 0.05 to 2 wt % (preferably, 0.1 to 1.5 wt %; more preferably, 0.25 to 1.25 wt %; most preferably, 0.5 to 1 wt %) of a processing aid; wherein the processing aid includes titanium dioxide.

Preferably, the personal cleansing soap bar composition of the present invention, further comprises: 0 to 0.5 wt % (preferably, 0.01 to 0.3 wt %; more preferably, 0.05 to 0.25 wt %; still more preferably, 0.075 to 0.2 wt %; most preferably, 0.1 to 0.15 wt %) of a chelating agent. More preferably, the personal cleansing soap bar composition of the present invention, comprises: 0.01 to 0.5 wt % (preferably, 0.05 to 0.25 wt %; more preferably, 0.075 to 0.2 wt %; most preferably, 0.1 to 0.15 wt %) of a chelating agent. Still more preferably, the personal cleansing soap bar composition of the present invention, comprises: 0.01 to 0.5 wt % (preferably, 0.05 to 0.25 wt %; more preferably, 0.075 to 0.2 wt %; most preferably, 0.1 to 0.15 wt %) of a chelating agent; wherein the chelating agent is selected from the group consisting of diethylenetriamine pentaacetic acid; 1-hydroxyethane 1,1-diphosphonic acid; citric acid; ethylene diamine tetraacetic acid (EDTA), salts thereof and mixtures thereof. Yet more preferably, the personal cleansing soap bar composition of the present invention, comprises: 0.01 to 0.5 wt % (preferably, 0.05 to 0.25 wt %; more preferably, 0.075 to 0.2 wt %; most preferably, 0.1 to 0.15 wt %) of a chelating agent; wherein the chelating agent is selected from the group consisting of diethylenetriamine pentaacetic acid pentasodium salt, 1-hydroxyethane 1,1-diphosphonic acid disodium salt; citric acid, ethylene diamine tetraacetic acid (EDTA), ethylene diamine tetraacetic acid tetrasodium salt and mixtures thereof. Most preferably, the personal cleansing soap bar composition of the present invention, comprises: 0.01 to 0.5 wt % (preferably, 0.05 to 0.25 wt %; more preferably, 0.075 to 0.2 wt %; most preferably, 0.1 to 0.15 wt %) of a chelating agent; wherein the chelating agent includes ethylene diamine tetraacetic acid tetrasodium salt.

Preferably, the personal cleansing soap bar composition of the present invention, further comprises: 0 to 10 wt % (preferably, 1 to 7.5 wt %; more preferably 2 to 6 wt %; most preferably, 3 to 5 wt %) of additional water (i.e., water in addition to that added as part of (a) the soap (e.g., as part of the soap noodles), (b) the aqueous dispersion comprising an ethylene acrylic acid copolymer; and (c) the silicone copolymer emulsion).

Preferably, the personal cleansing soap bar composition of the present invention, optionally further comprises at least one personal care ingredient. More preferably, the personal cleansing soap bar composition of the present invention, optionally further comprises at least one personal care ingredient; wherein the at least one personal care ingredient is selected from the group consisting of preservatives (e.g., benzoic acid, sorbic acid, phenoxyethanol); antioxidants (e.g., butylated hydroxytoluene); viscosity modifiers; fillers; foam stabilizers; foam enhancers; chelating agents; antimicrobial agents (e.g., biocides); pH adjusting agents; pH buffering agents; fragrances/perfumes; opacifying agents; salts and coloring agents (e.g., dyes). Most preferably, the personal cleansing soap bar composition of the present invention, optionally further comprises at least one personal care ingredient selected from the group consisting of a pH adjusting agent, a biocide, a fragrance and a colorant.

Preferably, the method of making the personal cleansing soap bar composition of the present invention, comprises: providing a soap; providing an aqueous dispersion comprising an ethylene acrylic acid copolymer; providing a silicone copolymer emulsion with an internal phase viscosity of $\geq 100 \times 10^6$ mm$^2$/sec; mixing the soap, the aqueous dispersion, and the silicone copolymer emulsion to form a combination; milling the combination; extruding the milled combination; and stamping the extruded material to provide the personal cleansing soap bar. More preferably, the method of making the personal cleansing soap bar composition of the present invention, comprises: providing soap noodles, wherein the soap noodles comprise $\geq 70$ wt % of total fatty material (TFM) and 10 to 15 wt % water; providing an aqueous dispersion comprising an ethylene acrylic acid copolymer; providing a silicone copolymer emulsion with an internal phase viscosity of $\geq 100 \times 10^6$ mm$^2$/sec; mixing the soap noodles, the aqueous dispersion, and the silicone copolymer emulsion to form a combination (preferably, heating the soap, the aqueous dispersion and the silicone copolymer emulsion while mixing to form the combination); milling the combination; extruding the milled combination; and stamping the extruded material to provide the personal cleansing soap bar.

Some embodiments of the present invention will now be described in detail in the following Examples.

Comparative Examples C1-C3 and Example 1:
Soap Bars

Soap bars were prepared having the composition noted in TABLE 1 for each of Comparative Examples C1-C3 and Example 1. Soap noodles were crushed in sigma mixer and mixed along with the other ingredients in the amounts noted in TABLE 1 in the sigma mixer. All ingredients were added sequentially with no specific order, except for the perfume, which was added last. The entire mass was then transferred from the sigma mixer to a triple roll mill to triturate the mixture. All the processes were carrier out under ambient conditions in the laboratory. The mass received from roll mill was then plodded in a screw plodder and extruded at a temperature of 45 to 55° C. The extruded mass was then cut into small pieces and punched in a soap die to provide the final product soap bars.

TABLE 1

| Component | (wt %) | | | |
|---|---|---|---|---|
| | Ex. C1 | Ex. C2 | Ex. C3 | Ex. 1 |
| Soap Noodles[1] | 92.50 | 92.50 | 92.50 | 92.50 |
| Glycerin | 1.00 | 1.00 | 1.00 | 1.00 |
| TiO$_2$ | 0.75 | 0.75 | 0.75 | 0.75 |
| Fragrance | 1.00 | 1.00 | 1.00 | 1.00 |
| Tetra sodium EDTA[2] | 0.12 | 0.12 | 0.12 | 0.12 |
| Treated Water | 4.63 | 4.03 | 4.03 | 4.03 |
| Ethylene/Acrylic Acid Dispersion[3] | — | 0.60 | — | 0.30 |
| Silicone copolymer Emulsion[4] | — | — | 0.60 | 0.30 |

[1]Wilfarin SN-8020 soap noodles available from Adani Wilmer Limited
[2]Versene (EDTA) 0.02% solution available from The Dow Chemical Company
[3]EcoSmooth ™ Satin aqueous ethylene acrylic acid copolymer dispersion available from The Dow Chemical Company
[4]DowSil ™ HMW 2220 silicone copolymer emulsion available from The Dow Chemical Company Soap Bar Performance Testing Ten trained panelists evaluated each of the soap bars prepared according to Comparative Examples C1-C3 and Example 1. The panelists each rated the bars on their perception of the sensory benefits of the bars based on a scale of 1-10 (higher number=better performance) for foam quality, foam quantity, rinseability, moisture feel, after wash feel and perfume retention. The averages for the results are provided in TABLE 2.

TABLE 2

| Ex | Foam Quality | Foam Volume | After Wash Feel | Rinseability | In Wash Feel | Moisture Feel |
|---|---|---|---|---|---|---|
| C1 | 5.5 | 5.7 | 5.5 | 5.6 | 5.3 | 5.4 |
| C2 | 6.9 | 7.2 | 7.2 | 6.7 | 7.0 | 7.3 |
| C3 | 7.0 | 7.6 | 7.1 | 7.0 | 7.3 | 7.1 |
| 1 | 7.8 | 7.9 | 7.9 | 7.9 | 8.3 | 8.4 |

The average performance for the personal cleansing soap bars of Example 1 having a synergistic combination of the aqueous ethylene acrylic acid copolymer dispersion and a silicone copolymer emulsion was highest in every sensory benefit category tested—foam quality, foam volume, after wash feel, rinseability, in wash feel and moisture feel. Moreover, the data was tabulated and analyzed using paired t test for mean comparison. The performance enhancement in the test data for the soap bars of Example 1 verses the comparison soap bars for both in wash feel and moisture feel was statistically significant (p-value≤0.015).

We claim:

1. A personal cleansing soap bar composition, comprising:
    60 to 90 wt % of a soap;
    0.25 to 0.35 wt % of an aqueous ethylene acrylic acid copolymer dispersion;
    0.25 to 0.35 wt % of a silicone copolymer emulsion with an internal phase viscosity at 25° C. of ≥120×10$^6$ mm$^2$/sec; wherein the silicone copolymer emulsion has an average particle size of <1 micron;
    wherein the personal cleansing soap bar is a solid.

2. The personal cleansing soap bar composition of claim 1, wherein the aqueous ethylene acrylic acid copolymer dispersion, comprises:
    an ethylene acrylic acid copolymer, comprising 15 to 30 wt %, based on weight of the ethylene acrylic acid copolymer, of structural units of acrylic acid; and 70 to 85 wt %, based on weight of the ethylene acrylic acid copolymer, of structural units of ethylene;
    a neutralizing agent and
    water;
    wherein at least some of the structural units of acrylic acid in the copolymer have been neutralized by the neutralizing agent.

3. The personal cleansing soap bar composition of claim 1, further comprising:
    0.1 to 5 wt % of a humectant;
    0.05 to 2 wt % of a processing aid;
    0.01 to 0.5 wt % of a chelating agent;
    0.1 to 10 wt % of additional water.

4. The personal cleansing soap bar composition of claim 1, wherein the silicone copolymer emulsion has an average particle size of less than or equal to 0.7 micron.

5. The personal cleansing soap bar composition of claim 4, wherein the silicone copolymer emulsion comprises:
    the silicone copolymer;
    at least one surfactant; and
    water.

6. The personal cleansing soap bar composition of claim 5, wherein the silicone copolymer emulsion contains 60 wt % silicone.

7. The personal cleansing soap bar composition of claim 6, wherein the silicone copolymer is an addition reaction product of: a polysiloxane with reactive groups on both termini and at least one silicone compound or non-silicone compound comprising an average of 1 to 2 moieties capable of reaction with the termini of the polysiloxane in the presence of a metal containing catalyst.

8. The personal cleansing soap bar composition of claim 7, wherein the polysiloxane has the following formula:

$$R_1-\underset{\underset{R_2}{|}}{\overset{\overset{R_2}{|}}{Si}}-O-\left[\underset{\underset{R_2}{|}}{\overset{\overset{R_2}{|}}{Si}}-O\right]_n-\underset{\underset{R_2}{|}}{\overset{\overset{R_2}{|}}{Si}}-R_1$$

wherein $R_1$ is a group capable of reacting by chain addition reaction; $R_2$ is selected from the group consisting of alkyl, cycloalkyl, aryl and alkylaryl; n is an average number selected such that the polysiloxane has a viscosity of 1 mm$^2$/sec to 1×10$^6$ mm$^2$/sec.

9. The personal cleansing soap bar composition of claim 1, further comprising at least one of: a pH adjusting agent, a biocide, a fragrance, a colorant and a soap.

10. A method of making a personal cleansing soap bar composition, comprising:
    providing a soap;

providing an aqueous dispersion comprising an ethylene acrylic acid copolymer;
providing a silicone copolymer emulsion with an internal phase viscosity of $>120 \times 10^6$ mm$^2$/sec and an average particle size of <1 micron;
mixing the soap, the aqueous dispersion, and the silicone copolymer emulsion to form a combination;
milling the combination;
extruding the milled combination; and
stamping the extruded material to provide the personal cleansing soap bar; wherein the personal cleansing soap bar comprises:
60 to 90 wt % of the soap;
0.25 to 0.35 wt % of the aqueous ethylene acrylic acid copolymer; and
0.25 to 0.35 wt % of the silicone copolymer emulsion.

* * * * *